United States Patent [19]

Holick et al.

[11] Patent Number: 5,037,816

[45] Date of Patent: * Aug. 6, 1991

[54] METHOD OF TREATING PSORIASIS

[75] Inventors: Michael F. Holick, Sudbary; Julia McLaughlin, Roxbury, both of Mass.

[73] Assignee: The General Hospital Corporation, Boston, Mass.

[*] Notice: The portion of the term of this patent subsequent to Mar. 1, 2005 has been disclaimed.

[21] Appl. No.: 136,207

[22] Filed: Dec. 21, 1987

Related U.S. Application Data

[62] Division of Ser. No. 667,813, Nov. 2, 1984, Pat. No. 4,728,643.

[51] Int. Cl.$^5$ .................... A61K 31/59; A61K 31/595
[52] U.S. Cl. ...................................... 514/167; 514/35; 514/168; 514/863
[58] Field of Search ................... 514/35, 167, 168, 803

[56] References Cited

U.S. PATENT DOCUMENTS

| | | | |
|---|---|---|---|
| 4,225,596 | 9/1980 | DeLuca | 514/167 |
| 4,230,701 | 10/1980 | Holick et al. | |
| 4,391,802 | 7/1983 | Suda et al. | |
| 4,410,515 | 5/1983 | Holick et al. | |
| 4,521,410 | 1/1985 | Holick et al. | |
| 4,588,716 | 3/1986 | DeLuca et al. | 514/168 |
| 4,610,978 | 9/1986 | Dikstein et al. | |
| 4,634,692 | 1/1987 | Partridge et al. | 514/167 |
| 4,719,205 | 1/1988 | DeLuca et al. | 514/167 |
| 4,728,643 | 3/1988 | Holick et al. | 514/167 |

FOREIGN PATENT DOCUMENTS

| | | |
|---|---|---|
| 129003 | 3/1984 | European Pat. Off. |
| 177920 | 10/1985 | European Pat. Off. |
| 55-111460 | 8/1980 | Japan ................................. 514/167 |
| 57-149224 | 9/1982 | Japan ................................. 514/167 |

OTHER PUBLICATIONS

Holick, M. F., et al., "The New England Journal of Medicine", vol. 303, pp. 349-354 (1980).

MacLaughlin, J., et al., "9th Intl'l Congress on Photobiology & 12th Ann. Mtg. Amer. Soc. Photobiol." 1984 Abstract MAM-D5.

Hosomi, J., et al., "Endocrinology", vol. 3, pp. 1950-1957 (1983).

Clemens, T. L., et al., "Journal of Clinical Endorcinology and Metabolism" vol. 56, pp. 824-830 (1983).

Honma, Y., et al., "Proc. Natl. Acad. Sci.", vol. 80, pp. 201-204 (1983).

Shina, Y., et al., "Archives of Biochemistry and Biophysics", vol. 220, pp. 90-94 (1983).

Dikstein, Shabtay, "Chem. Abstracts", vol. 102, p. 119663.

Holick, M., "The Photobiology of Vitamin D3 in Man", pp. 197-216 (1984).

Morimoto, S., "Chemical Abstracts", vol. 106:23300u.

van de Kerkhof, P. C. M. et al., *Br. J. Dermatol* 210:661-664 (1989).

Morimoto, S. et al., *Br. J. Dermatol.* 115:421-429 (1986).

Morimoto, S. et al., *Med. J. Osaka Univ.* 35:51-54 (1985).

Morimoto, S. et al., *Calcif. Tissue Int.* 38:119-212 (1986).

Harrison's, *Principles of Internal Medicine*, Braunwald et al., (eds), McGraw-Hill Book Co., N. Y., 1460-1461, Tenth Edition.

Matsumoto, T. et al., *J. Biol. Chem.* 256:3354-3360 (1981).

Englavish, A. et al., *J. Membrane Biol.* 72:85-91 (1983).

Nemere, I. et al., *Endocrinology* 115:1476-1483 (1984).

(List continued on next page.)

Primary Examiner—H. M.S. Sneed
Assistant Examiner—J. Saba
Attorney, Agent, or Firm—Sterne, Kessler, Goldstein & Fox

[57] ABSTRACT

A method of treating psoriasis in a patient which comprises administering to said patient an effective amount of a vitamin D compound which is capable of stimulating the differentiation of cultured tumor cells or normal rodent or human fibroblasts or keratinocytes in vitro.

15 Claims, 2 Drawing Sheets

OTHER PUBLICATIONS

Karsenty, G. et al., *Am. J. Physiol.* 248:G40 (1985).
Edelman, A. et al., *J. Membrane Biol.* 90:137–143 (1986).
Brasitus, T. A. et al., *J. Biol. Chem.* 261:16404–16409 (1986).
Kurnik, B. R. C. et al., *Biochim. Biophys. Acta* 858:47–55 (1986).
Tang, W. et al., *J. Cell Physiol.* 132:131–136 (1987).
Hruska, K. A. et al., *J. Biol. Chem.* 263:16039–16044 (1988).
Lieberberr, M. et al., *J. Biol. Chem.* 34:20403 (1989).
MacLaughlin, J. A. et al., *J. Nutr. Biochem.* 1:81–87 (1990).
van Bokhoven, M. G. J. et al., *Br. J. Dermatol.* 119:737–742 (1988).
*Official Gazette* 1108 No. 1, p. 7, Reissue Notice for Re. 33,107.

METHOD OF TREATING PSORIASIS

This application is a division of application Ser. No. 667,813, filed Nov. 2, 1984 now U.S. Pat. No. 4,728,643.

BACKGROUND OF THE INVENTION

1. Field of the Invention

The present invention relates to a novel method of treating psoriasis, a disease of the skin. The method comprises using vitamin D-related compounds.

2. Brief Description of the Background Art

Psoriasis is a disease of the epidermis and a major cause of disability and disfigurement for between 2,000,000 and 8,000,000 persons in the U.S. Of these, about 100,000 are severely affected.

The disease is diagnosed by the presence of scaling erythematous on the scalp and extender aspects of the arms and legs; psoriatic lesions often are accentuated on the sites of repeated trauma, such as the elbows and knees. The papules or plaques of psoriasis often contain a silvery-white micaceous scale that is relatively easily removed in layers. There is a several fold increase in the normal number of the basal cells of the epidermis. This increase in the basal cell population reduces the turnover time of the epidermis from the normal 27 days to 3-4 days. This shortened interval leads to the consequence that normal events of cell maturation or keratinization do not occur, and this failure of maturation is reflected by an array of abnormal morphologic and biochemical changes. Numerous cytologic, histologic, histochemical and biochemical alterations are now known to be the result, rather than the cause of the disease process. The only main fact known at this time about the fundamental cause of psoriasis is that the predisposition to its development is genetically transmitted. (This introduction is basically taken from Harrison's *Principles of Internal Medicine*, 10th Ed., Vol. 1, pp. 256 and 257).

The treatment of psoriasis still remains the province of dermatologists. The most effective treatment in the control of localized psoriasis for most patients is the topical use of corticosteroids with a plastic wrap and ultraviolet light or sunlight exposures. On certain patients who have generalized psoriasis, it has been necessary to use a variety of systemic chemotherapeutic agents, especially methotrexate; the latter has the capacity to inhibit cell replication without a proportionate inhibition of cell function; i.e. keratinization. Photochemotherapy was introduced in 1974, in the so-called PUVA treatment. In this treatment, psoralen is administered two hours before total body irradiation with a special light system that emits predominantly long wave ultraviolet light. The light alone is ineffective in producing erythema or remission of psoriatic lesions; however, in the presence of one of the psoralens, the UV-A light becomes a potent photoactive agent and produces a remission of psoriatic lesions after several exposures. Photochemotherapy requires specialized knowledge and lighting systems delivering precisely measured amounts of ultraviolet light.

Along quite different areas of research, Holick et al. (*New England Journal of Medicine*, 303: 349-354 (1980)) have studied the feasibility of using the skin as the organ for the synthesis and absorption of vitamin D metabolites. These investigators demonstrated that topical application of various vitamin D metabolites or provitamin forms followed by phototherapy results in elevated serum levels of dihydroxy-vitamin $D_3$. It was therefore suggested that topical application of vitamin D analogues may be an effective method of therapy for diseases involving calcium, phosphorus and bone metabolism problems. It is only recently, however, that it has become clear that the skin itself may be a target tissue for 1,25-$(OH)_2$-$D_3$ (Stumpf, W.E. et al. *Science*, 206:1188-1190 (1979)). Cells isolated from the skin of rats, mice, and humans, and from cultured human skin fibroblasts and keratinocytes contain a high affinity (1.0 x $10^{-10}$ M) low capacity receptor-like protein for 1,25-dihydroxy-vitamin $D_3$ (Franceschi, et al., *Arch. Biochem. Biophys.*, 210: 1-13 (1979); Simpson, R. U. et al., *P.N.A.S. U.S.A.*, 77: 5822 (1980); Colston, K. et al., *Endocrinology*, 107: 1916 (1980); Feldman, D. et al., *Journal of Clinical Endocrinology & Metabolism*, 51: 1463 (1980); Eil, C. et al., *P.N.A.S. U.S.A.*, 78: 2562 (1981); and Clemens, T. L. et al., *J. Clin. Endocr. Metab.* 56: April 1983). A specific biological function for 1,25-$(OH)_2$-vitamin $D_3$ in the skin, however, has yet to be discovered. Nevertheless, evidence has come forth supporting the concept that the dihydroxy metabolite of the vitamin does have biologic actions in the skin. This was accomplished by evaluating the biological activity of 1,25-dihydroxy-$D_3$ simultaneously in cultured human skin fibroblasts that either possessed or lacked a cytosolic receptor-like protein for the hormone (Clemens, T. L. et al., *J. Clin. Endocrinol. Metab.*, 56:April 1983). The receptor-negative skin fibroblasts were obtained from a patient with a rare bone disorder called vitamin D dependent rickets, type II, a heritable disorder caused by a defective or complete absence of a cytoplasmic or nuclear receptor for 1,25-dihydroxy vitamin D. The dihydroxy metabolite of vitamin $D_3$ caused a dose-dependent inhibition of cell growth in receptor positive skin fibroblasts (about 40-50% reduction in cell growth was observed in cultures containing $10^{-6}$ and $10^{-8}$ M of hormone and 12% in cultures containing $10^{-10}$ M of 1,25-$(OH)_2$-$D_3$), and, by contrast, had absolutely no effect on the growth of receptor negative skin fibroblasts.

The aforementioned seemingly two divergent lines of research, the treatment of psoriasis on the one hand, and the effects of vitamin $D_3$ on skin components on the other, remained heretofore unrelated until, by the present invention, they have been brought together.

SUMMARY OF THE INVENTION

This invention arose out of the initial observation that when psoriatic cells were incubated in vitro with 1,25-$(OH)_2$-$D_3$ at physiologic concentrations, they were resistant to growth inhibition effects, whereas at pharmacologic concentrations ($10^{-6}$ and $10^{-4}$ M), the dihydroxy metabolite of vitamin $D_3$ was capable of inhibiting the cell growth of these psoriatic fibroblasts. Thus vitamin D, as well as its homologues, analogues and hydroxylated metabolites, can be utilitized effectively in the treatment of psoriasis.

An accurate correlation between an in vitro test or tests and anti-psoriatic treatment in vivo has further been established. According to this correlation, the vitamin D compounds usable in the treatment of psoriasis are those capable of stimulating or inducing the differentiation of tumor or normal cell lines which possess receptors for 1,25-dihydroxyvitamin $D_3$. Normal cell lines include cultured rodent and human keratinocytes. Active compounds are also those capable of increasing the enzymatic activity of transglutaminase in the same cell system, or are those capable of inhibiting the cell growth in vitro of human skin fibroblasts. Details of these tests can be found below.

The vitamin D compounds, homologues, analogues or metabolites thereof which are useful in treating psoriasis are those which demonstrate activity in any of the in vitro tests.

DESCRIPTION OF THE PREFERRED EMBODIMENTS

Figure 1A:
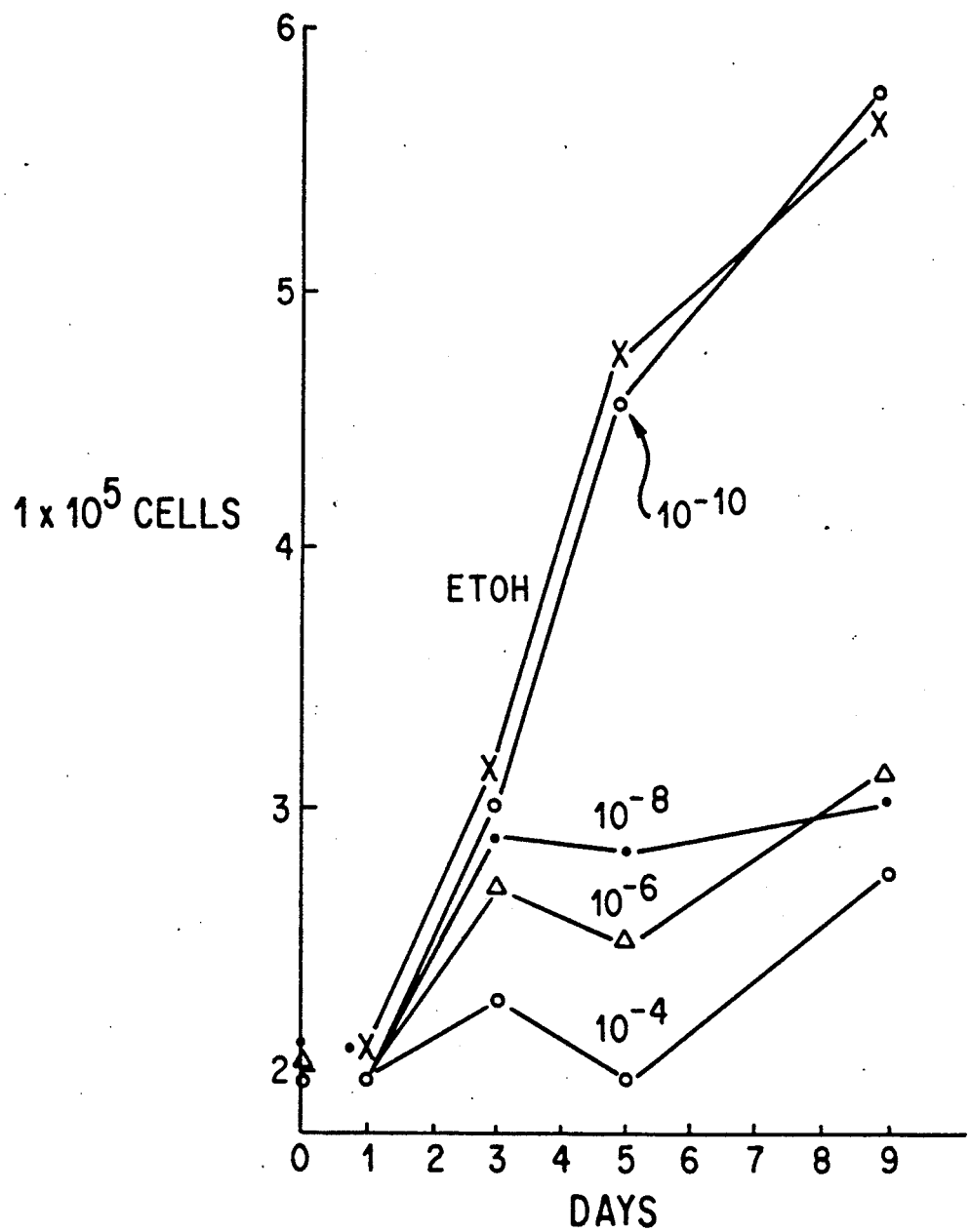
FIG. 1 depicts the effect of different concentrations of $1\alpha$, 25-dihydroxyvitamin $D_3$ on the inhibition of fibroblast growth, wherein the cultured human fibroblasts were obtained from normal (A, control) and psoriatic (B) subjects.

Generally, an active compound is one which induces differentiation at physiologic concentration of a tumor or a normal cell line which possess receptors for 1,25-dihydroxyvitamin $D_3$. Among normal useable lines are for example human or rodent keratinocytes or fibroblasts. Among tumor lines are HL-60 cell line, M-1 cell line, breast tumor cells. A few tests will be described in further detail herein.

A first test is one which measures the differentiation of cultured keratinocytes. The assay is essentially the one described by Hosomi, et al., "Regulation of Terminal Differentiation of Cultured Mouse Epidermal Cells by $1\alpha$,25-dihydroxy Vitamin $D_3$," *Endocrinology*, 113: 1950 (1983) for mice, or that described by Clemens et al. supra for the human system, both herein incorporated by reference. Briefly, epidermal cells are prepared from newborn C57BL mice by overnight treatment with trypsin at 4° C. followed by separation of the epidermis from the dermis with forceps. Cells are plated at a density of $10^6$ cells per 4.5 cm² well and grown in Eagle minimum essential medium (MEM) (supplemented with 10% fetal calf serum (FCS)). Cells can also be grown in low calcium medium, Eagle MEM, without calcium supplemented with 10% dialyzed FCS. Calcium concentration of the low calcium medium can be from about 0.01–0.5 mM, whereas a conventional MEM plus 10% FCS usually may contain 1.0–2.0 mM calcium. Cells are incubated in a humidified $CO_2$ incubator at 37° C. All experiments are performed on the primary cultures. Twenty-four hours after plating, the medium is changed and the vitamin D compound is added at concentration of 0.12, 1.2 and 12 nm (0.05, 0.5 and 5.0 mg/ml, respectively). Control cultures are supplemented with ethanol at a final concentration of 0.5%. The media with and without the vitamin D is renewed every 3–4 days. (FCS contains 1,25-$(OH)_2$-$D_3$ at 0.12 nm (Tanaka, H. et al. *Biochem. J.*, 204: 713 (1982)). Therefore, the endogenous concentration of the vitamin in the control culture medium which contains 10% FCS is negligible.)

Differentiation of epidermal cells in culture is examined morphologically by (1) counting the number of squamous and enucleated cells sloughed off into the medium,
(2) counting the number of squamous and basal cells attached to the dishes,
(3) formation of a cornified envelope,
(4) the cell size and cell density, or
(5) morphological changes seen under a light microscope, or some or all of the above in combination.

Floating cells are collected from the medium. Then the cultures are washed with phosphate buffered saline (PBS) and attached cells are dissociated by treatment with 0.05% trypsin and 0.1% EDTA solution at 37° C. for 20–30 min. Cell suspensions are then divided into two portions: one for counting the numbers of squamous and basal cells and the other for counting cornified envelopes. Since basal cells are small and round, whereas squamous and enucleated cells are large and flat, they are readily distinguishable in a hemocytometer. The method of Sun and Green (Cell, 9: 511 (1976)) can be used to determine the presence of a cornified envelope. The cells are resuspended in 10 mM Tris-HCl (pH 7.4) containing 1% beta-mercaptoethanol and 1% sodium dodecylsulfate at a density of $5:30 \times 10^4$ cells/ml. The mixture stands for 10 minutes at room temperature and then insoluble cells are counted in a hemocytometer under a phase contrast microscope.

The size of cells can be measured in photographs with a stage micrometer as a standard. The density distribution of cells is measured by density gradient centrifugation in Percoll$^R$. Epidermal cells $8\text{-}11 \times 10^6$/ml are suspended in PBS containing 40% Percoll, placed in a 10 ml polycarbonate tube, and centrifuged at $15,000 \times g$ at 3° C. for 30 minutes in an angled rotor. Fractions are collected by use of density marker beads. For light microscopic observation, cells grown in a glass cover slip are fixed with either 10% formalin or methanol/acetic acid (3:1) and stained with hemotoxiline and eothine or rhodanile blue.

In the presence of an active vitamin D compound useful for psoriatic treatment, differentiation of epidermal cells is markedly stimulated. Focal stratification is formed in places on top of the epidermal cell sheets. Stratified foci increase in number and size and contiguous foci coalesce. In the uppermost layer of stratified foci, cells produce an amorphous material staining red with hemotoxaline and eothine and rhodanile blue. Some cells are enucleated and some have a thick pycnoctic nucleus. Differentiated cells slough off into the medium so that the total number of cells attached to the dish decrease continuously with the time of cultivation. The fraction of attached basal cells decrease sharply in the presence of an active vitamin D compound. For example, close to 100% of the cells are basal cells on day 0, but only about 25% on day 3 and less than 10% after day 10. In a control culture on the other hand, more than 60% of the cells are basal cells during the first six days and usually 30–40% or so remain basal on day 10. In parallel with decrease of basal cells, the number of squamous cells increases in the vitamin D active treated cultures, first among the attached cell population and then among the sloughed off floating cells.

Epidermal differentiation can be quantified by counting cornified envelopes remaining after cell lysis with a solution containing 1% sodium dodecylsulfate and 1% beta-mercaptoethanol. When the cells are grown in the presence of 12 nM active vitamin D compound, the percentage of cells with a cornified envelope increases with time of cultivation. The percentage is greatest after 10 days in culture when about 60–70% of the cells have an envelope. In contrast, the percentage of control cultures remain at 20% or less during a two week observation period.

The cells obtained in the presence of an active vitamin D compound for 3 days are larger and lighter than those in its absence. The diameter of cells in the treated cultures is usually about 25±10 mm, compared with about 17±5 mm in a control.

Cell density by Percoll gradient centrifugation indicates that, when grown in the presence of an active vitamin D compound for 3 days, about 65% of the cells are collected in the lightest fraction with a density of about 1.017-1.027, whereas about 40% of the control cells are recovered in this fraction. Concomitantly, the number of cells in a heavier fraction (density) between about 1.06 and 1.08 decrease in the treated cultures. Similar results are obtained at day 7. Human keratinocytes can be grown by the method of Clemens et al., supra, and analyzed in an identical manner.

A second test is that of inhibition of human skin fibroblasts. This test is found in Clemens et al., *J. Clin. Endocr. Metab.*, 56: 824 (1983), herein incorporated by reference. Briefly, skin cells are isolated from surgically obtained normal human skin from mammary, face, thigh, etc. of a normal patient.

Normal skin biopsies are placed immediately in Dulbecco's modified Eagle's medium (DMEM) containing 10% fetal bovine serum, penicillin G (75 U/ml), and streptomycin (50 ng/ml). After removal of subcutaneous fat and the deep reticular layer of the dermis, the tissues are minced and placed in 10 ml 0.25% trypsin at 4° C. overnight.

Fibroblasts are plated at $7-10 \times 10^4$ cells in 35-mm Costar dishes in DMEM containing 5% NBS. After attachment of cells (6 hours), the media are aspirated and replaced with fresh medium containing ethanol alone (0.01%) or ethanol (0.01%) containing compound at $10^{-10}$, $10^{-8}$, $10^{-6}$, or $10^{-4}$ M. At intervals thereafter, cells are harvested from duplicate plates by trypsinization and counted in a Coulter counter. Control and compound supplemented media are replaced at 4-day intervals. Normal foreskin fibroblasts, plated at $5 \times 10^4$ cells/well (DMEM; 5% NBS), can also be treated with ethanol (0.01%) alone or ethanol containing compound $10^{-10}$-$10^{-4}$ M). After 4 days, fresh medium containing the appropriate sterol is replaced, and cells are counted 2 days later, 6 days after plating.

An alternative and perhaps faster and more accurate test of correlation for active vitamin D compounds is the in vitro activity of transglutaminase, in the keratinocyte culture. The enzymatic test is carried out according to standard transglutaminase assays, Scott, K.F.F. et al., *J. Cell. Physiol.* 111:111-116 (1982). Any compound which when present at a concentration of $10^{-12}$M to $10^{-3}$ M increases the enzymatic activity by 25% or more, preferably 50% or more, most preferably 100% or more is considered an active compound.

Use of the HL-60 cells in an in vitro test is described in Shiina, et al., *Arch. Biochem. Biophys.* 220:90 (1983). Use of the M1 cells in an in vitro test is described in Honma et al., *PNAS, USA* 80:201-204 (1983). Both of these references are herein incorporated by reference.

Any vitamin D compound which at in vitro concentrations of $10^{-12}$ M to $10^{-3}$ M is capable of cellular differentiation or inhibiting of fibroblast growth by at least 25%, preferably 50% is considered active.

Among the preferred compounds usable in the present invention are those of the formula (I):

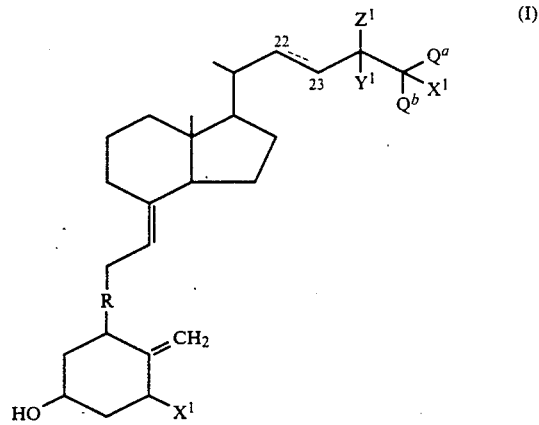

wherein the bond between carbons C-22 and C-23 is single or double; $Y^1$ is hydrogen, F, —$CH_3$ or —$CH_2CH_3$;

$Z^1$ is F, H or $X^1$;

$Q^a$ is $CF_3$ or $CH_2X^1$;

$Q^b$ is $CF_3$ or $CH_3$;

R is a double bond or an epoxy group;

wherein X is selected from the group consisting of hydrogen and —OH.

When the compounds of formula (I) have a double bond at position C-22, they are derivatives of vitamin $D_2$, whereas if the bond at that position is single, and there is a lack of $C_{24}$ alkyl, they are derivatives of vitamin $D_3$. The latter are preferred.

Preferred are those compounds derived from vitamins mins $D_3$ or $D_2$;1-hydroxy-vitamins $D_3$ or $D_2$; 1,25-dihydroxy vitamins $D_3$ and $D_2$; 24,25-dihydroxy vitamins $D_3$ or $D_2$; 25,26-dihydroxy vitamins $D_3$ or $D_2$; 1,24,25-trihydroxy vitamins $D_3$ or $D_2$. Most preferred among these are vitamins $D_3$ or $D_2$; 1-hydroxy-vitamins $D_3$ or $D_2$; and 1,25-dihydroxy-vitamins $D_3$ or $D_2$, especially 5,6-epoxy derivatives of vitamin D and its metabolites, as well as the side chain fluoro derivatives of 1, 25-$(OH)_2$ vitamin D and 1 (OH) vitamin D.

Among other preferred compounds are water soluble derivatives of the aforementioned compounds of formula (I) obtained by solubilizing such compounds by attaching thereto glycosidic residues such as those disclosed in Holick, U.S. Pat. No. 4,410,515. Alternative methods of solubilization are by conjugating compounds of formula (I) to glycosyl orthoester residues, as disclosed in copending U.S. S.N. 607,117 by Holick et al., filed May 3, 1984. The disclosures of the aforementioned patent and application are herein incorporated by reference and made a part hereof.

Of interest are compounds of the formula (II):

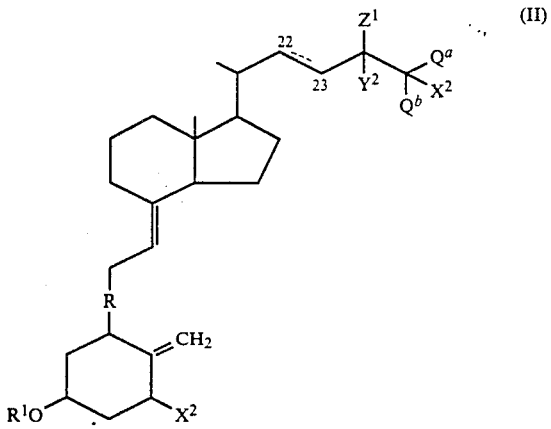

(II)

wherein $Y^2$ is hydrogen, fluorine, methyl or ethyl;
$Z^2$ is F, H or $X^2$
$Q^a$ and $Q^b$ have the same meanings as in formula (I);
R is a double bond or an epoxy group;
$X^2$ is selected from the group consisting of hydrogen, and $OR^1$,
where $R^1$ is hydrogen or a straight or branched chain glycosidic residue containing 1-20 glycosidic units per residue, or $R^1$ is an ortoester glycoside moiety of the formula (III).

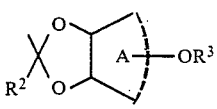

(III)

where A represents a glucofuranosyl or glucopyranosyl ring;
$R^2$ is hydrogen, lower alkyl, aralkyl, or aryl; and
$R^3$ is hydrogen or a straight or branched chain glycosidic residue containing 1-20 glycosidic units per residue, with the proviso that at least one of the $R^1$ is either a glycosidic residue or an orthoester glycoside moiety.

The vitamin D compounds are prepared or obtained according to the disclosures of the aforementioned references. In particular, the 5,6-epoxy derivatives of vitamin $D_3$ are obtained as described in *Jpn. Kokai Tokkyo Koho* JP 58,216,178 [83,216,178], Dec. 15, 1983.

The fluoro derivatives are made or obtained as described in Shiina, et al., *Arch. Biochem. Biophys* 20:90 (1983).

The compounds of the invention can be administered in any appropriate pharmacological carrier for oral, parenteral, or topical administration. They can be administered by any means that effects palliating conditions of psoriasis in humans. The dosage administered will be dependent upon the age, health and weight of the recipient, kind of concurrent treatment, if any, frequency of treatment and the nature of the effect desired. Generally, systemic daily dosage of active ingredient compounds will be from about 0.001 micrograms/kg to 100 micrograms/kg preferably 0.1 to 1.0 micrograms per kg of body weight. Normally, from 0.1 to 100 micrograms/kg per day, in one or more applications per day is effective to obtain the desired results. Topical dosage would be 0.001 micrograms to 100 micrograms/$cm^2$ area of skin.

The compounds can be employed in dosage forms such as tablets, capsules, powder packets, or liquid solutions, suspensions or elixirs for oral administration, sterile liquid for formulations such as solutions or suspensions for parenteral use. Alternatively, the compounds can be present in a pharmacologically inert topical carrier such as one comprising a gel, an ointment or a cream, including such carriers as water, glycerol, alcohol, propylene glycol, fatty alcohols, triglycerides, fatty acid esters or mineral oils. Other possible carriers are liquid petrolatum, isopropylpalmitate, polyethylene glycol ethanol 95%, polyoxyethylene monolaurate 5% in water, sodium lauryl sulfate 5% in water, and the like. Materials such as anti-oxidants, humectants, viscosity stabilizers and the like may be added, if necessary.

The compounds can also be administered by means of pumps or tapes.

Having now generally described this invention, the same will be understood by reference to an example which is provided herein for purposes of illustration only and is not intending to be limited unless otherwise specified.

EXAMPLE

Skin biopsies from involved and uninvolved sites were obtained from psoriatic patients and therefrom were obtained cultured fibroblasts. An analysis of cultured fibroblasts from the psoriatic patients revealed that these possess high affinity low capacity receptors for 1,25-$(OH_2)$-$D_3$ and that the Kd and density for these receptors in fibroblasts from the uninvolved areas were essentially no different from that found in cultured skin fibroblasts from normal subjects. In addition, the fibroblasts from involved sites possessed receptors for 1,25-dihydroxyvitamin $D_3$ that have a normal affinity constant but possibly as much as 100% decrease in number of receptor sites when compared to the uninvolved fibroblasts.

Figure 1B:
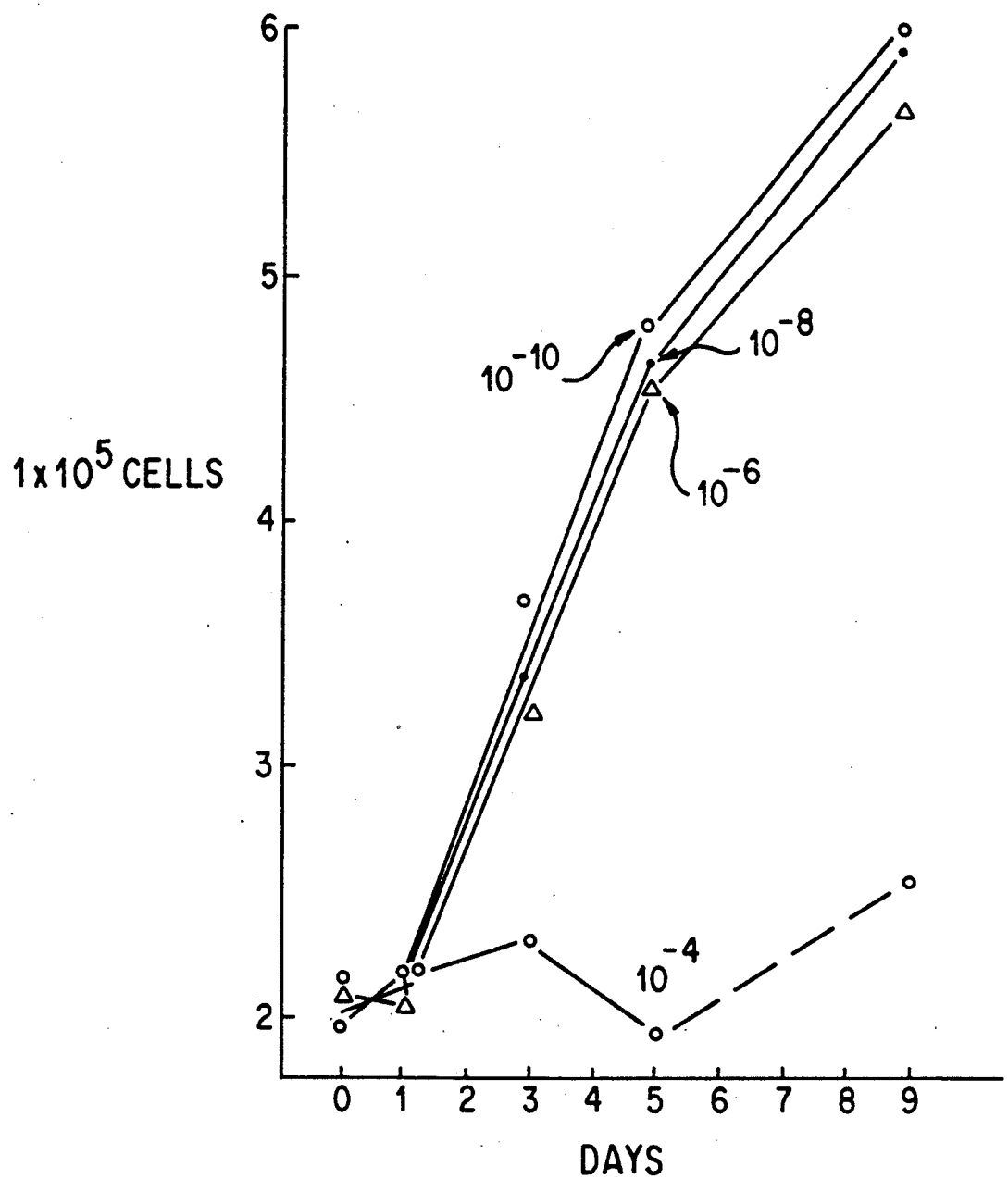

It was next determined if cultured fibroblasts from psoriatic patients would respond to 1,25-dihydroxyvitamin $D_3$ by causing an inhibition of cell growth. Cultured human fibroblasts from normal and psoriatic subjects were incubated with either no 1,25-dihydroxyvitamin $D_3$ or 1,25-dihydroxy vitamin $D_3$ at either $10^{-10}$, $10^{-8}$, $10^{-6}$, or $10^{-4}$ M. Fibroblasts from the normal subjects responded as expected in a dose dependent manner. However, none of the fibroblasts obtained from six different subjects with psoriasis responded to 1,25-dihydroxyvitamin $D_3$ at $10^{-8}$ M in a similar fashion as the controls. When psoriatic cells were incubated with 1,25-$(OH)_2$-$D_3$ at $10^{-6}$ M, there was a small but significant effect on inhibiting cell growth in some of the subjects studied (who were resistant to up to $10^{-6}$ M of 1,25-dihydroxy vitamin $D_3$). In one subject, a detailed time course and dose response revealed a very small response at $10^{-6}$ M while 1,25-dihydroxy vitamin $D_3$ at $10^{-4}$ M was very effective in inhibiting cell growth (FIG. 1).

What is claimed as new and desired to be covered by U.S. Letters Patent is:

1. A method of treating the disease of psoriasis in a patient affected by said disease which comprises administering to said patient an effective amount of a vitamin D compound by topical means, which compound when tested in vitro is capable of stimulating the differentiation of cells selected from the group consisting of:
   (a) cultured tumor cells, and
   (b) cultured normal rodent or human keratinocytes or fibroblasts;

wherein said vitamin D compound has the formula (I):

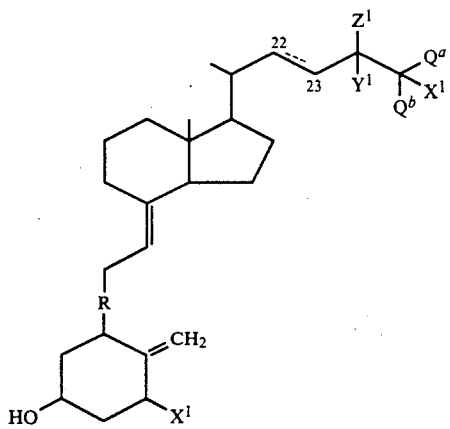

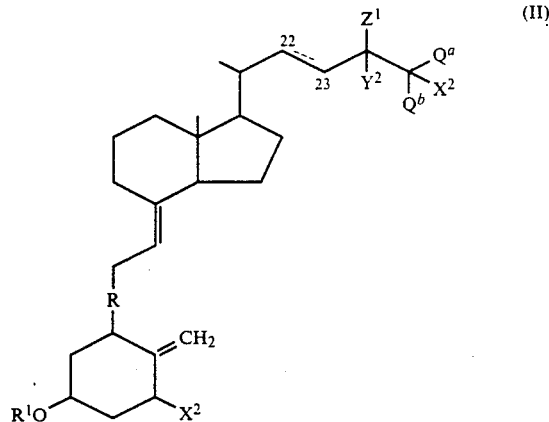

wherein the bond between carbons C-22 and C-23 is a single or double bond; $Y^1$ is hydrogen, F, $CH_3$, or $CH_2CH_3$;

$Z^1$ is F, H or $X^1$;
$Q^a$ is $CF_3$ or $CH_2X^1$;
$Q^b$ is $CF_3$ or $CH_3$;
R is a double bond or an epoxy group;
wherein $X^1$ is selected from the group consisting of hydrogen and —OH; with the proviso that where:
  (1) said bond between carbons C-22 and C23 is a single bond and
  (2) $X^1$ is hydroxyl
then at least one of the group consisting of $Y^1$, $Z^1$, $Q^a$ and $Q^b$ contains a fluorine atom or $Z_1$ is OH or $Q^a$ is —$CH_2$OH.

2. The method of claim 1 wherein said vitamin D compound has the formula (I) and wherein said bond between carbons C-22 and C-23 is a single bond and wherein $X^1$ is hydrogen.

3. The method of claim 1 wherein said vitamin D compound has the formula (I) and wherein said bond between carbons C-22 and C-23 is a single bond and $X^1$ is hydroxyl and at least one of the group consisting of $Y^1$, $Z^1$, $Z^a$ and $Q^b$ contains a fluorine atom.

4. The method of claim 1 wherein said vitamin D compound has the formula (I) and wherein said bond between carbons C-22 and C-23 is a double bond.

5. The method of claim 1 wherein said vitamin D compound has the formula (I) and wherein said bond between carbons C-22 and C-23 is a double bond and $X^1$ is hydrogen.

6. The method of claim 1 wherein said vitamin D compound has the formula (I) and wherein said bond between carbons C-22 and C-23 is a double bond and $X^1$ is hydroxyl.

7. A method of treating the disease of psoriasis in a patient affected by said disease which comprises administering to said patient an effective amount of a vitamin D compound by topical means, which compound when tested in vitro is capable of stimulating the differentiation of cells selected from the group consisting of:
  (a) cultured tumor cells, and
  (b) cultured normal rodent or human keratinocytes or fibroblasts;
wherein said vitamin D compound has the formula (II):

wherein the bond between carbons C-22 and C-23 is a single or double bond; $Y^2$ is hydrogen, fluorine, methyl, or ethyl;
$Z^2$ is F, H or $X^2$;
$Q^a$ is $CF_3$ or $CH_2X^2$;
$Q^b$ is $CF_3$ or $CH_3$;
R is a double bond or an epoxy group;
$X^2$ is selected from the group consisting of hydrogen, and $OR^1$,
wherein $R^1$ is hydrogen or a straight or branched chain glycosidic residue containing 1–20 glycosidic units per residue, or $R^1$ is an orthoester glycoside moiety of the formula (III):

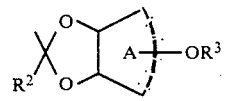

wherein A represents a glucofuranosyl or gluocopyranosyl ring;
R2 is hydrogen, lower alkyl, aralkyl, or aryl; and
$R^3$ is hydrogen or a straight or branched chain glycosidic residue containing 1–20 glycosidic units per residue, with the proviso that at least one of the $R^1$ is either a glycosidic residue or an orthoester glycoside moiety and with the proviso that where said bond between carbons C-22 and C-23 is a single bond, at least one of the group consisting of $Y^1$, $Z^1$, $Q^a$ and $Q^b$ contains a fluorine atom.

8. The method of claim 7 wherein said vitamin D compound has the formula (II) and wherein said bond between carbons C-22 and C-23 is a single bond and wherein at least one of the group consisting of $Y^1$, $Z^1$, Qhu a and $Q^b$ contains a flluorine atom.

9. The method of any one of claims 1 and 7 wherein said cells are cultured tumor cells.

10. The method of claim 9 wherein said cultured tumor cells are human tumor cells.

11. The method of claim 10 wherein said human tumor cells are selected from the group consisting of:
  (a) HL-60 cells, and
  (b) M-1 cells.

12. The method of any one of claims 1 and 7 wherein said cells are cultured normal rodent or human keratinocytes or fibroblasts.

13. The method of any one of claims 1 and 7 wherein said vitamin D compound is capable, when tested in vitro, or inhibiting the growth of normal fibroblast growth.

14. The method of claim 13 wherein said fibroblasts are human.

15. The method of claim 1, wherein said vitamin D compound is 1,25-dihydroxyvitamin $D_2$.

* * * * *